(12) United States Patent
Shih et al.

(10) Patent No.: US 8,501,214 B2
(45) Date of Patent: Aug. 6, 2013

(54) HYDROPHILIC FOAM AND PHARMACEUTICAL DOSAGE FORM EMPLOYING THE SAME

(75) Inventors: Ming-Kuang Shih, Sinjhuang (TW); Yu-Chou Chao, Taipei (TW); Jenn-Line Sheu, Hsinchu (TW); Ying-Chu Shih, Jhubei (TW)

(73) Assignee: Modetex Biomedical Materials & Technology Industrial Corp., Sinjhuang, Taipei County (TW)

( * ) Notice: Subject to any disclaimer, the term of this patent is extended or adjusted under 35 U.S.C. 154(b) by 750 days.

(21) Appl. No.: 12/651,293

(22) Filed: Dec. 31, 2009

(65) Prior Publication Data

US 2010/0104642 A1    Apr. 29, 2010

Related U.S. Application Data

(63) Continuation-in-part of application No. 12/323,008, filed on Nov. 25, 2008, now abandoned.

(60) Provisional application No. 60/990,174, filed on Nov. 26, 2007.

(51) Int. Cl.
*A61F 2/00* (2006.01)

(52) U.S. Cl.
USPC .......................................... 424/425; 424/424

(58) Field of Classification Search
USPC ................................................. 424/424, 425
See application file for complete search history.

(56) References Cited

U.S. PATENT DOCUMENTS

| | | | | |
|---|---|---|---|---|
| 5,556,612 | A | * | 9/1996 | Anderson et al. ............... 424/59 |
| 5,902,603 | A | * | 5/1999 | Chen et al. .................... 424/449 |
| 6,348,212 | B2 | * | 2/2002 | Hymes et al. ................. 424/449 |
| 2003/0181415 | A1 | | 9/2003 | Zaneveld et al. |
| 2009/0137661 | A1 | | 5/2009 | Shih et al. |

* cited by examiner

*Primary Examiner* — San-Ming Hui
(74) *Attorney, Agent, or Firm* — Muncy, Geissler, Olds & Lowe, PLLC

(57) ABSTRACT

Disclosed herein is a hydrophilic foam. The hydrophilic foam includes a polyurethane matrix having a plurality of cells. The cells are capable of retaining water in an amount of least about 8 grams of water per gram of the hydrophilic foam.

4 Claims, 3 Drawing Sheets

HYDROPHILIC FOAM AND PHARMACEUTICAL DOSAGE FORM EMPLOYING THE SAME

RELATED REFERENCE

This application is a continuation-in-part of U.S. patent application Ser. No. 12/323,008 filed on Nov. 25, 2008 now abandoned and entitled "Plant Derived Compounds And Compound Formulae Containing The Same For The Treatment Of Cervical Cancer", which claims priority to U.S. Provisional Patent Application No. 60/990,174, filed on Nov. 26, 2007 and entitled "Plant Derived Compounds And Compositions Thereof For Inhibiting The Activity Of Human Papilloma Virus", the entire disclosures of which are incorporated herein by reference.

BACKGROUND

1. Field of Invention

The present invention relates to hydrophilic foams and a pharmaceutical dosage form employing the same. More particularly, the present invention relates to the pharmaceutical dosage form for treating, managing or preventing vaginal infections or cervical cancer.

2. Description of Related Art

Vaginitis (vaginal infections) is a vaginal inflammation that results in discharge, odor, pain, or itching, and often associated with an irritation or infection of the vulva. The most common vaginal infections include bacterial vaginosis, vaginal yeast infection, trichononiasis and viral infection. Viral infections are among the hardest to treat. Moreover, human papilloma virus (HPV) infection may cause cervical cancer.

These infections may have similar symptoms, especially in the early stage of the disease development, yet their treatment varies. Medications for treating and/or managing these vaginal infections may be provided in single unit dosage forms suitable for oral, parenteral (e.g., subcutaneous, intravenous, bolus injection, or intramuscular), or transdermal (including mucosal, such as viginal) administration to a patient.

Active agents contained in the parenterally or orally administered medications are often absorbed by the liver which phenomenon is known as the first-pass effect of the liver. Transdermally administering the active agents, on the other hand, may avoid the first-pass effect because it allows the active agents to be absorbed directly into the systemic circulation.

In treating and/or managing the vaginal infections or cervical cancer, the transdermal administration is often targeted at vaginal or cervical tissues. For example, vaginal suppositories, creams, ointments, or gels are often inserted into the vagina with a plunger-type applicator or applied onto the membrane of the vagina by other means. However, the walls of the vagina are composed of soft elastic folds of mucous membrane; hence it is difficult to the make the medication adherent to and/or evenly distributed across the membrane without hurting or damaging the membrane.

Accordingly, there exists a need in the related art for a better pharmaceutical dosage form for treating, managing or preventing vaginal infections or cervical cancer.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present invention is directed to a hydrophilic foam.

According to one embodiment of the present invention, the hydrophilic foam comprises a polyurethane matrix having a plurality of cells. The cells are capable of retaining water in an amount of at least about 8 grams of water per gram of the hydrophilic foam.

In another aspect, the present invention is directed to a composition for preparing a hydrophilic foam.

According to one embodiment of the present invention, the composition comprises a blowing agent composition consisting of water in an amount of 1 part by weight, and at least one hydrophilic polyol in an amount of about 22-40 parts by weight, based on 1 part by weight of water; an isocyanate in an amount of about 10 to 15 parts by weight; a catalyst in an amount of about 0.01 to 0.1 part by weight; a chain extender in an amount of about 0.05 to 0.1 part by weight; and a foam stabilizer in an amount of about 0.1 to 1 part by weight, all based on 1 part by weight of water.

In still another aspect, the present invention is directed to a aquagel composition capable of reducing the viral activity of a human papilloma virus in a virus-infected cell or a virus-infected subject.

According to one embodiment of the present disclosure, the aquagel composition may comprise a gel matrix present in the aquagel composition in an amount of about 0.01-10 ppm. The gel matrix is at least one of: tragacanth gum, pectin, alginic acid, xanthan gum, mamnnan oligosaccharide, guar gum, gelatin, carrageenan, chondroitin sulfate, glucan sulfate, sodium carboxymethylcellulose, carboxyethyl cellulose, carboxymethyl chitin, and agar.

In yet another aspect, the present invention is directed to a transdermal pharmaceutical dosage form for treating, managing or preventing vaginal infections or cervical cancer.

According to one embodiment of the present invention, the transdermal pharmaceutical dosage form comprises a hydrophilic foam comprising a polyurethane matrix having a plurality of cells, wherein the hydrophilic foam has a gel retention rate of about 1-25 grams of gel per gram of the hydrophilic foam; and a gel retained within the cells of the hydrophilic foam, wherein the gel comprises an effective amount of at least one active agent.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein.

DETAILED DESCRIPTION

Figure 1:
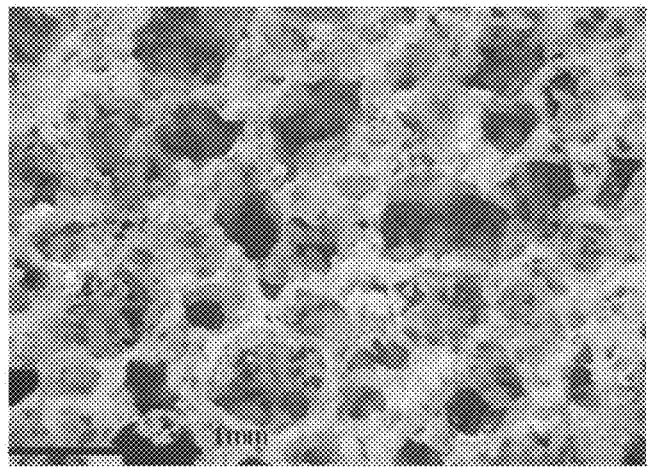
FIG. 1 is a 40× microphotograph illustrating a portion of the hydrophilic foam of one working examples according to the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

One purpose of the present application is to develop a pharmaceutical dosage form suitable for treating, managing or preventing vaginal infections or cervical cancer. In particular, the pharmaceutical dosage form is targeted at vaginal so as to avoid the first-pass effect. Desirably, the pharmaceutical dosage form may release the active agent(s) in a quick yet sustained way. Besides, the pharmaceutical dosage form should be allergic-free and bio-compatible.

The preliminary idea is to provide a matrix that is suitable for inserting into the vaginal canal and also capable of absorbing/retaining active agent(s) therein and releasing active agent(s) therefrom. The sanitary tampon at first is regarded as a candidate. However, commercially available sanitary tampons may not release the active agent(s) in a desired way. Another candidate is polyurethane (PU) sponges. Nevertheless, commercially available PU sponges usually have undesirable air permeability; hence, the PU sponges, when being inserted into the vaginal canal, may cause uncomfortable feelings.

Accordingly, in one aspect, the present invention is directed to a hydrophilic foam. The hydrophilic foam exhibits desired air permeability, water and gel retention rates, and elasticity. Moreover, the cells of the hydrophilic foam are arranged in such a way that they form a continuous phase so that the hydrophilic foam, when being used as a vehicle for delivering active agent(s), is able to release the active agent(s) in a quick yet sustained way.

According to one embodiment of the present invention, the hydrophilic foam comprises a polyurethane matrix having a plurality of cells. The cells are capable of retaining water in an amount of least about 8 grams of water per gram of the hydrophilic foam.

In the present disclosure, the ability of the cells to retain water (or gel) may sometimes be referred to as the "water (or gel) retention rate" of the hydrophilic foam.

According to some embodiments, the cells of the hydrophilic foam are capable of retaining water in an amount of about 10-20 grams of water per gram of the hydrophilic foam. For example, the water retention rate of the hydrophilic foam may be about 10, 11, 12, 13, 14, 15, 16, 17, 18, 19, or 20 grams of water per gram of the hydrophilic foam. In the present disclosure, the water retention rate of the hydrophilic foam is also presented as the percentage of the weight of the hydrophilic foam. For example, a hydrophilic foam having a water retention rate of about 1674% means that the hydrophilic foam may retain 16.74 grams of water per gram of the hydrophilic foam. Similarly, a hydrophilic foam capable of retaining water in an amount of least about 8 grams of water per gram of the hydrophilic foam may have a water retention rate of 800%.

Gels, in addition to water, may also be retained in the cells of the hydrophilic foam according to the present disclosure. The gel retention rate may vary with the composition and physical properties (such as viscosity and hydrophilicity) of the gel. The gel can be an aquagel (hydrogel) or an oil-in-water (O/W) gel. Generally, the viscosity of the gel is in a range of about 100-5000 cps. According to some embodiment of the present disclosure, the cells of the hydrophilic foam are capable of retaining such gel in an amount of about 1-25 grams of gel per gram of the hydrophilic foam. For example, the gel retention rate of the hydrophilic foam may be about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15.5, 16, 16.5, 17, 17.5, 18, 18.5, 19, 19.5, 20, 20.5, 21, 21.5, 22, 22.5, 23, 23.5, 24, 24.5, or 25 grams of gel per gram of the hydrophilic foam. In one working example presented hereinafter, the hydrophilic foam has a gel retention rate of about 22.02 grams of gel per gram of the hydrophilic foam, wherein the viscosity of the gel is about 402 cps.

The process and composition for preparing the hydrophilic foam are also provided in the present disclosure. According to the present disclosure, the hydrophilic foam obtained by the process and from the composition may have at least one of the properties specified in the above-mentioned aspect/embodiments of the present disclosure.

According to one embodiment of the present invention, the composition comprises a blowing agent composition consisting of water in an amount of 1 part by weight, and at least one hydrophilic polyol in an amount of about 22-40 parts by weight, based on 1 part by weight of water; isocyanate in an amount of is about 10 to 15 parts by weight, a catalyst in an amount of about 0.01 to 0.1 part by weight, a chain extender in an amount of about 0.05 to 0.1 part by weight; and a foam stabilizer in an amount of about 0.1 to 1 part by weight; all based on 1 part by weight of water.

The blowing agent composition according to the present disclosure consists of water and polyol; that is, water is used as the sole blowing agent in such composition. Conventionally, the composition for preparing a polyurethane sponge may contain an organic blowing agent such as trichlorofluoromethane and dichloromethane. However, such blowing agents may be hazardous to human health which renders them less favorable for preparing a medication vehicle. Hence, the present disclosure provides a novel composition excluding such toxic blowing agent(s).

According to the principles and spirits of the present disclosure, the polyol used in the composition may preferably be a hydrophilic polyol. Examples of the polyol include, but are not limited to, polyoxypropylene glyceryl ether and polyoxyethylene polyoxypropylene glyceryl ether.

Moreover, the hydrophilic polyol should be used in an amount so that the composition may be properly foamed under the action of water in the absence of organic blowing agents such as dichloromethane. Accordingly, in the blowing agent composition, the polyol and the water are present in a weight ratio of about 22 to about 40. For example, the weight ratio of the polyol to the water is about 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or 40. Preferably, the hydrophilic polyol and the water are present in a weight ratio of about 25-40. In one working example provided hereinafter, the polyol is polyoxyethylene polyoxypropylene glyceryl ether, and the weight ratio of the polyol to the water is about 36.5.

Generally, the polyurethane matrix having a plurality of cells is the product of the polymerization of the isocyanate and polyol. Examples of isocyanate include, but are not limited to, 4,4'-diphenylmethane diisocyanate (MDI), toluene diisocyanate (TDI), 3,3'-diphenylmethane diisocyanate, isophorone diisocyanate, 4,4'-dicyclohexylmethane diisocyanate, and hexamethylene diisocyanate. In one optional embodiment of the present disclosure, the isocyanate used in the composition is MDI.

The amount of the isocyanate in the composition may be in a range of about 10 to 15 parts by weight based on 1 part by weight of water in the composition. For example, the weight ratio of the isocyanate to the water is about 10, 10.5, 11, 11.5, 12, 12.5, 13, 13.5, 14, 14.5, or 15.

Catalyst used in the composition is capable of catalyzing the polymerization of the isocyanate and polyol. Suitable catalyst includes, but is not limited to metal carboxylates (eg., dibutyl tin dilaurate or stannous octoate) and tertiary amine such as N-methyl morpholine, N-ethyl morpholine, triethylamine, dimethylbenzylamine, triethylene diamine, hexadecyl dimethylamine, N,N,N',N'-tetramethyl-1,3-butanediamine, N,N-dimethylethanolamine, bis(2-dimethylaminoethyl)ether, and N,N,N'N'-tetramethylethylenediamine. In one optional embodiment of the present disclosure, the catalyst used in the composition is N-ethyl morpholine.

The amount of the catalyst in the composition may be in a range of about 0.01 to 0.1 parts by weight based on 1 part by weight of water in the composition. For example, the weight ratio of the catalyst to the water is about 0.01, 0.02, 0.03, 0.04, 0.05, 0.06, 0.07, 0.08, 0.09, or 0.1.

The chain extender may be a low molecular weight branched or unbranched diol, diamine or aminoalcohol of up to 10 carbon atoms or mixtures thereof. Examples of the chain extender includes but are not limited to ethylene glycol, diethylene glycol, triethylene glycol, 1,2-propanediol, 1,3-propanediol, 1, 6-hexanediol, trimethylol propane, 1,4-bis-hydroxymethyl cyclohexane, hydroquinone dihydroxyethyl ether, ethanolamine, diethanolamine, ethylenediamine, hexamethylenediamine and 2 methyl-pentamethylene diamine.

The amount of the chain extender in the composition may be in a range of about 0.05 to 0.1 parts by weight based on 1 part by weight of water in the composition. For example, the weight ratio of the chain extender to the water is about 0.05, 0.06, 0.07, 0.08, 0.09, or 0.1.

Foam stabilizers are usually surfactants. According to the embodiments of the present disclosure, any surfactant as known in the foam art may be used, such as the polyoxyethylene ethers and esters of the TRITON® and TWEEN® series. Silicone surfactants may also be used as the foam stabilizer in the composition.

The amount of the foam stabilizer in the composition may be in a range of about 0.1 to 1 parts by weight based on 1 part by weight of water in the composition. For example, the weight ratio of the foam stabilizer to the water is about 0.1, 0.2, 0.3, 0.4, 0.5, 0.6, 0.7, 0.8, 0.9, or 1.

According to the embodiments of the present disclosure, the process for preparing the hydrophilic foam may comprise the steps as follows.

First, the constituents of the above-mentioned composition are admixed in the specified amount. Then, the composition is extrusion molded and allowed for foaming. The foaming step may be carried out at about 100° C. for about 1-10 seconds. Thereafter, the product is aged so as to yield the hydrophilic foam of the present disclosure. The product is aged at an ambient temperature (about 23-27° C.) for a period of about 5-10 days.

Some working examples according to embodiments of the present disclosure and comparative examples are provided hereinafter. In those examples, various compositions were employed to prepared PU sponges, and the PU sponges thus-obtained were tested for some physical properties such as the water and/or gel retention rate, the air permeability, and the elasticity thereof. In addition, bio-compatibility of the hydrophilic foam of the working examples was also analyzed.

Constituents of the compositions for preparing the working and comparative examples are summarized in Table 1.

TABLE 1

| | | |
|---|---|---|
| Working Example 1 | Polyol (wt %) | Polyoxypropylene glyceryl ether (22) + Polyoxyethylene polyoxypropylene glyceryl ether (50.9) |
| | Blowing agent (wt %) | Water (2) |
| | Isocyanate | MDI (24) |
| | Catalyst (wt %) | N-ethyl morpholine (0.08) |
| | Chain extender (wt %) | Diethanolamine (0.12) |
| | Foam stabilizer (wt %) | Silicone surfactant (0.9) |
| Working Example 2 | Polyol (wt %) | Polyoxyethylene polyoxypropylene glyceryl ether (72.9) |
| | Blowing agent (wt %) | Water (2) |
| | Isocyanate | MDI (24) |
| | Catalyst (wt %) | N-ethyl morpholine (0.08) |
| | Chain extender (wt %) | Diethanolamine (0.12) |
| | Foam stabilizer (wt %) | Silicone surfactant (0.9) |
| Comparative Example A | Polyol (wt %) | Polyether triol (70.5) |
| | Blowing agent (wt %) | Water (2) + Dichloromethane (2.6) |
| | Isocyanate | TDI (22.3) |
| | Catalyst (wt %) | N-ethyl morpholine (0.4) + Stannous octoate (1) |
| | Foam stabilizer (wt %) | Silicone surfactant (1.2) |
| Comparative Example B | Polyol (wt %) | Polyoxypropylene glyceryl ether (66.12) |
| | Blowing agent (wt %) | Water (2) + Dichloromethane (5.8) |
| | Isocyanate | MDI (22.1) |
| | Catalyst (wt %) | N-ethyl morpholine (0.08) |
| | Chain extender (wt %) | Diethanolamine (0.3) |
| | Foam stabilizer (wt %) | Silicone surfactant (0.8) |
| | Cell regulator (wt %) | Methypolysiloxane (2.8) |
| Comparative Example C | Polyol (wt %) | Polyoxypropylene glyceryl ether (45) + Polyoxyethylene polyoxypropylene glyceryl ether (24.8) |
| | Blowing agent (wt %) | Water (2) + Dichloromethane (2.9) |
| | Isocyanate | MDI (22.8) |
| | Catalyst (wt %) | N-ethyl morpholine (0.08) |
| | Chain extender (wt %) | Diethanolamine (0.12) |
| | Foam stabilizer (wt %) | Silicone surfactant (0.9) |
| | Cell regulator (wt %) | Methypolysiloxane (1.4) |

The composition of comparative example A is one of the commercially available polyurethane sponges. The compositions of comparative examples B and C are proposed during the process of developing the hydrophilic foam of the present disclosure. Yet, the physical properties of comparative examples B and C are not qualified for use as the pharmaceutical dosage form according to another aspect of the present disclosure.

By comparing the working examples with the comparative examples, it is found that when the weight ratio of the polyoxyethylene polyoxypropylene glyceryl ether to the water is greater than 25, the polymerization product of the composition may be properly foamed under the action of water as the sole blowing agent. In addition, as the amount of the polyoxyethylene polyoxypropylene glyceryl ether increases, the amount of the MDI should increase accordingly.

Figure 2:
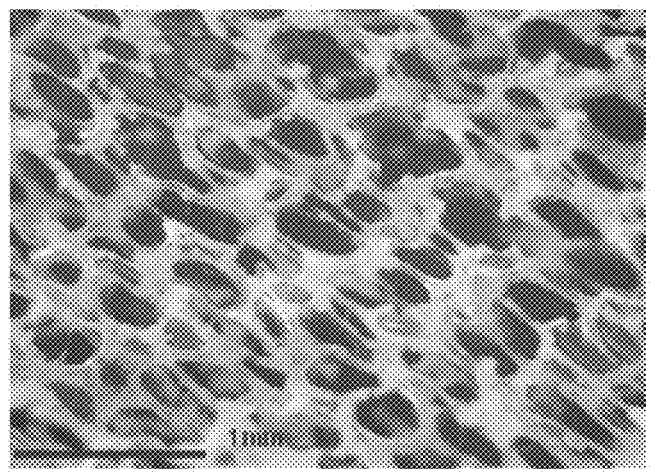
FIG. 2 is a 40× microphotograph illustrating a portion of the hydrophilic foam of another working example according to the present disclosure.

FIG. 1 and FIG. 2 are 40× microphotographs illustrating a portion of the hydrophilic foam of the working examples 1 and 2, respectively. As depicted in FIG. 2, the cells of the hydrophilic foam form a continuous phase which renders it a candidate for use as a medication vehicle.

Some physical properties of the polyurethane sponges of each working and comparative examples are summarized in Table 2.

TABLE 2

| | Density (g/cm$^3$) | Water retention rate (%) | Air permeability (sec) | Rebound time (sec) | Porosity (pores/cm$^2$) |
|---|---|---|---|---|---|
| Working Example 1 | 0.058 | 1104 | 8.9 | <1 | 3400 |
| Working Example 2 | 0.033 | 1674 | 1.7 | <1 | 5700 |
| Comparative Example A | 0.06 | 254.4 | 34.6 | — | — |
| Comparative Example B | 0.02 | 390 | 29.9 | — | — |
| Comparative Example C | 0.01 | 600 | 30.3 | — | — |

The density, water retention rate, air permeability, and rebound time were respectively determined in accordance with IS-103-NSP-002, IS-103-NSP-001, IS-103-NSP-003, IS-103-NSP-005 standards specified by Industrial Technology Research Institute of Taiwan, ROC.

In the present disclosure, as the water retention rate of the hydrophilic foam increases, so is the degree of skin-friendliness of the hydrophilic foam. Hydrophilic foam for used as the medication vehicle according to the present to disclosure are desirably to be skin-friendly so that the pharmaceutical dosage form containing the same, when being inserted into the vaginal canal, would not cause uncomfortableness. As depicted in Table 2, a significant improvement of the water retention rate can be observed by comparing the working examples and the comparative examples.

Air permeability is carried in accordance with the protocol set forth in CNS 12915 Method B. The result is expressed in terms of the time required for 300 mL of air to pass through the sample of an area of 6.4 mm$^2$ at pressure of 141.8 gf. As such, a sample with a shorter pass-through time would possess a better air permeability. Air permeability is also positively related to the skin-friendliness of the hydrophilic foam. The air permeability of the hydrophilic foam of the present disclosure also improves considerably.

The rebound time is related to the elasticity of the hydrophilic foam. The rebound times of the hydrophilic foams of the working examples are less than 1 second, which renders the hydrophilic foams suitable for use as the medication vehicle of the pharmaceutical dosage form of the present disclosure.

The hydrophilic foams of the working examples 1 and 2 were tested for the sensitization and hemocompatibility. The sensitization test was carried out in accordance with the modified ISO 10993-10 standard to test the sensitivity to chemical extractables from medical devices. None of the tested Wistar mice showed positive response to the test materials. The hemocompatibility was carried out in accordance with ISO 10993-4 standard for the assessment of medical devices and their constituent materials with regard to their potential to produce irritation and delayed-type hypersensitivity. According to the test results, the hemolytic index of the hydrophilic foams is 0, which means non-hemolytic.

In still another aspect, the present invention is directed to a aquagel composition capable of reducing the viral activity of a human papilloma virus in a virus-infected cell or a virus-infected subject.

According to one embodiment of the present disclosure, the aquagel composition may comprise a gel matrix, wherein the gel matrix is at least one of: tragacanth gum, pectin, alginic acid, xanthan gum, mamnnan oligosaccharide, guar gum, gelatin, carrageenan, chondroitin sulfate, glucan sulfate, sodium carboxymethylcellulose, carboxyethyl cellulose, carboxymethyl chitin, and agar. The gel matrix is present in the aquagel composition in an amount of about 0.01-10 ppm. For example, the amount of the gel matrix may be about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.5, 2, 2.5, 3, 3.5, 4, 4.5, 5, 5.5, 6, 6.5, 7, 7.5, 8, 8.5, 9, 9.5, or 10 ppm.

In some optional embodiments, the aquagel composition may further comprise a hyaluronic acid present in the aquagel composition in an amount of about 0.01-4.5 ppm, for example, about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, and 0.45 ppm.

In some optional embodiments, the aquagel composition may further comprise a propylene glycol present in the aquagel composition in an amount of about 0.05-25 ppm. In particular, the amount of the aquagel composition is about 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or 25 ppm.

In some optional embodiments, the aquagel composition may further comprise a buffer present in the aquagel composition in an amount such that the aquagel composition has a pH of about 3-5, wherein the buffer is at least one of citric acid, tartaric acid, lactic acid, and salts thereof. The pH of the aquagel composition may be about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.

In some optional embodiments, the aquagel composition may further comprise an emulsifier present in the aquagel composition in an amount of about 0.0009-6.5 ppm. The amount of the emulsifier is about 0.0009, 0.001, 0.005, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, or 6.5 ppm.

In some optional embodiments, the aquagel composition may further comprise an oil present in the aquagel composition in an amount of about 0.02-40 ppm. In various examples, the oil is at least one of grape seed oil, olive oil, Camellia oil, apricot oil, peanut oil, maize oil, hydrogenated vegetable oil, castor oil, and silicone oil. The amount of the oil is about 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, or 45 ppm.

In the following working examples, an aquagel was prepared in accordance with the present disclosure. The aquagel was diluted to different concentration and tested for the efficacy for reducing the viral activity of a human papilloma virus in a virus-infected cell or a virus-infected subject.

The MTT assay, screening platform and screening method were similar to those described in U.S. patent application Ser. No. 12/323,008 (filed on Nov. 25, 2008 and entitled "Plant Derived Compounds And Compound Formulae Containing The Same For The Treatment Of Cervical Cancer"). In the following experiments, the signal to noise ratio is 0.66.

According to the first experiment, the aquagel composition of aquagel A comprises: about 2.5 wt % alginic acid, about 0.5 wt % hyaluronic acid, about 6 wt % propylene glycol, and about 91 wt % water.

The aquagel A was diluted with various amount of water to obtain the aquagel compositions containing the aquagel A in an amount of about 0.0003 wt %, 0.0008 wt %, 0.0025 wt % and 0.025 wt %, respectively.

Figure 3:
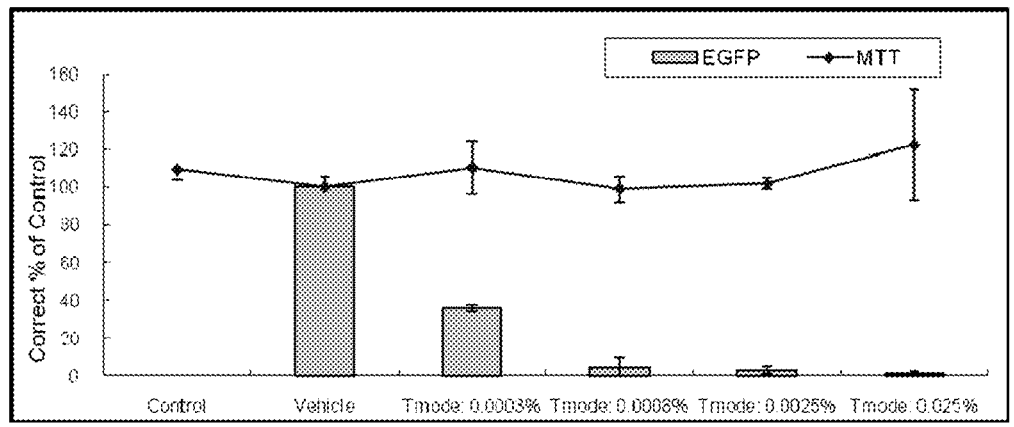
FIG. 3 is a graph illustrating the relationship between the concentrations of the aquagel A and the HeLa cell survival rate (shown as line in the graph) and HPV 16 pseudovirus infection rate (shown as blocks in the graph) at 48 hours after treatment according to one experiment of the present disclosure.

The aquagel compositions containing various amounts of aquagel A were added in the well for the screening and MTT assay, and the results are summarized in Table 3 and are shown in FIG. 3.

Figure 4:
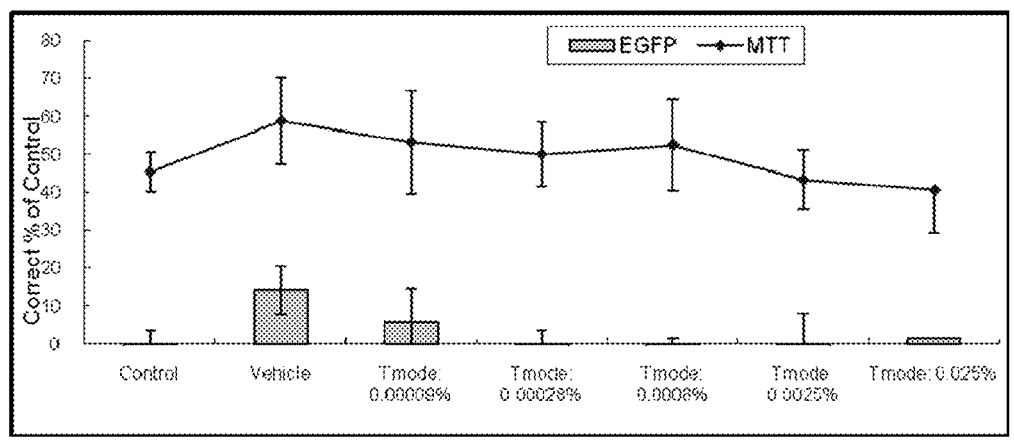
FIG. 4 is a graph illustrating the relationship between the concentrations of the aquagel A retained in a hydrophilic foam pad and the HeLa cell survival rate (shown as line in the graph) and HPV 16 pseudovirus infection rate (shown as blocks in the graph) at 48 hours after treatment according to one experiment of the present disclosure.

In the second experiment, the aquagel A was diluted with various amount of water to obtain the aquagel compositions containing the aquagel A in an amount of about 0.00009 wt %, 0.00028 wt %, 0.0008 wt %, 0.0025 wt % and 0.025 wt %, respectively. Meanwhile, the hydrophilic foam of working example 2 was cut into pads of about 1.2-1.5 mg. The pads were pretreated by being soaked in 70% EOH for 20 minutes and then baked at 56° C. for 80 minutes. About 10 μl of the aquagel composition was pipetted into each pad; after that, the pad was put in the well for the screening and MTT assay, and the results are summarized in Table 3 and are shown in FIG. 4.

According to the third experiment, the aquagel composition of aquagel B comprises: about 2.5 wt % carrageenan, about 0.5 wt % hyaluronic acid, about 6 wt % propylene glycol and about 91 wt % water.

The aquagel B was diluted with various amount of water to obtain the aquagel compositions containing the carrageenan in an amount of about 0.04, 0.12, 0.37 or 1.1 ppm, respectively.

Figure 5:
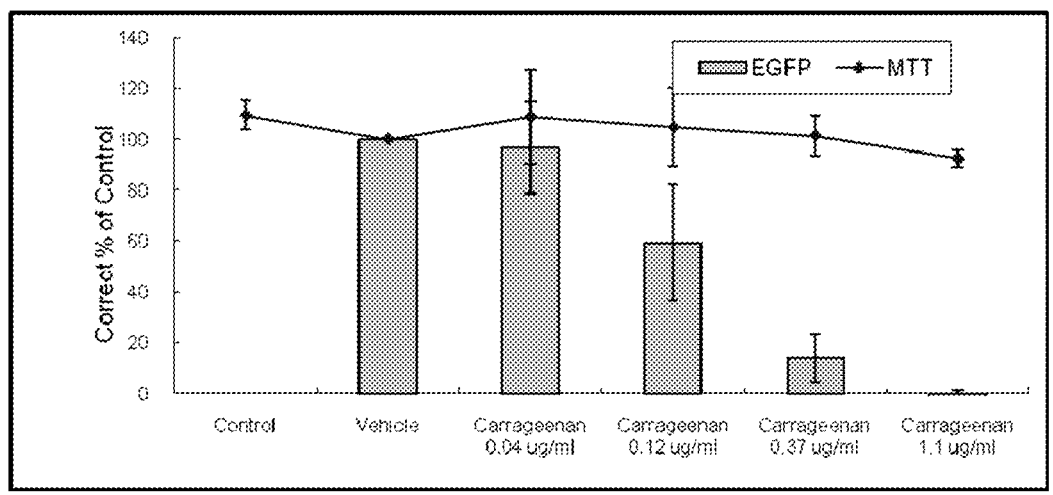
FIG. 5 is a graph illustrating the relationship between the concentrations of the aquagel B and the HeLa cell survival rate (shown as line in the graph) and HPV 16 pseudovirus infection rate (shown as blocks in the graph) at 48 hours after treatment according to another experiment of the present disclosure.

The aquagel compositions containing various amounts of carrageenan were added in the well for the screening and MTT assay, and the results are summarized in Table 3 and are shown in FIG. 5.

TABLE 3

| | Correct % of Control | | | |
| | MTT | | EGFP | |
| | Average | S.D. | Average | S.D. |
| Experiment 1 | | | | |
| Control | 109.43 | 5.64 | 0.00 | 0.00 |
| Vehicle | 100.00 | 0.00 | 100.00 | 0.00 |
| Aquagel A: 0.00009% | 96.91 | 4.60 | 206.90 | 79.83 |
| Aquagel A: 0.0003% | 110.24 | 14.32 | 35.65 | 1.97 |
| Aquagel A: 0.0008% | 98.92 | 6.79 | 4.36 | 5.00 |
| Aquagel A: 0.0025% | 101.84 | 3.02 | 3.09 | 2.22 |
| Aquagel A: 0.025% | 122.34 | 29.22 | 1.12 | 0.91 |
| Experiment 2 | | | | |
| Control | 45.35 | 5.17 | −2.20 | 5.38 |
| Vehicle | 58.81 | 11.42 | 13.95 | 6.43 |
| Aquagel A: 0.00009% | 53.18 | 13.65 | 5.59 | 8.84 |
| Aquagel A: 0.00028% | 49.97 | 8.58 | −1.53 | 4.80 |
| Aquagel A: 0.0008% | 52.45 | 12.01 | −3.49 | 4.83 |
| Aquagel A: 0.0025% | 43.23 | 7.99 | −3.99 | 11.80 |
| Aquagel A: 0.025% | 40.49 | 11.20 | 1.32 | 3.71 |
| Experiment 3 | | | | |
| Control | 109.43 | 5.64 | 0.00 | 0.00 |
| Vehicle | 100.00 | 0.00 | 100.00 | 0.00 |
| Carrageenan 0.04 ug/ml | 108.93 | 18.46 | 96.80 | 18.05 |
| Carrageenan 0.12 ug/ml | 104.79 | 15.27 | 59.12 | 22.86 |
| Carrageenan 0.37 ug/ml | 101.40 | 7.96 | 13.84 | 9.54 |
| Carrageenan 1.1 ug/ml | 92.38 | 3.26 | −2.10 | 3.37 |

The data shown in Table 3 are expressed in terms of corrected percentage of control. All data were compared in relative to the data of the vehicle of experiment 1.

From the data shown in Table 3 and FIG. 3 to FIG. 5, it is obtained that the $IC_{50}$ of the aquagel A of the experiment 1 for reducing the viral activity of a human papilloma virus is smaller than 0.75 ppm, whereas the $IC_{50}$ of carrageenan of the experiment 2 for reducing the viral activity of a human papilloma virus is about 0.15 ppm.

In addition, the aquagel of the experiment B also exhibits the ability for reducing the viral activity of a human papilloma virus. Hence, it is established that the hydrophilic foam of the present disclosure is capable of releasing the gel retained therein.

In yet another aspect, the present invention is directed to a transdermal pharmaceutical dosage form for treating, managing or preventing vaginal infections or cervical cancer.

According to one embodiment of the present invention, the a transdermal pharmaceutical dosage form comprises a hydrophilic foam comprising a polyurethane matrix having a plurality of cells, wherein the cells are capable of retaining a gel in an amount of about 1-25 grams of gel per gram of the hydrophilic foam; and a gel retained within the cells of the hydrophilic foam, wherein the gel comprises an effective amount of at least one active agent.

In view of the foregoing discussion, the polyurethane matrix according to the first aspect of the present disclosure is suitable for use as the medication vehicle of such transdermal pharmaceutical dosage form.

The gel retention rate of the hydrophilic foam may vary with the composition and physical properties (such as viscosity and hydrophilicity) of the gel. The gel can be an aquagel (hydrogel) or an oil-in-water (O/W) gel. Generally, the viscosity of the gel is in a range of about 100-5000 cps, and the hydrophilic foam is capable of retaining such gel in an amount of about 1-25 grams of gel per gram of the hydrophilic foam.

In particular, the viscosity of the gel may be about 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 cps. Besides, the gel retention rate of the hydrophilic foam may be about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15.5, 16, 16.5, 17, 17.5, 18, 18.5, 19, 19.5, 20, 20.5, 21, 21.5, 22, 22.5, 23, 23.5, 24, 24.5, or 25 grams of gel per gram of the hydrophilic foam.

In the working examples provided hereinafter, aquagels and O/W gels with various compositions and viscosities were prepared. Hydrophilic foam of working examples 1 and 2 were used to determine the gel retention rates thereof. The gel retention rate was determined in accordance with the procedure set forth in the above-mentioned IS-103-NSP-001.

The aqua gels were composed mainly of water, polyethylene glycol (PEG), adjuvant (alginic acid) and hydroxyethylcellulose (HEC). O/W gels were composed of water, 3-Mix oil (grape seed oil: olive oil: Camellia oil=1:1:1), aqua oil, alginic acid MD 12 having a molecular weight in the range of 50,000-100,000 Da, and optionally, PEG. The weight ratios of the constituents were adjusted to afford aquagels and O/W gels with various viscosities. About 2 wt % citric acid was added into the gel in an amount such that the pH of the gel was maintained at about 4-5. The viscosities of the gels and results of the gel retention test are summarized in Table 3. In Table 3, the Hydrophilic foam of working examples 1 and 2 are referred to as hydrophilic foam 1 and hydrophilic foam 2, respectively.

TABLE 3

| Gel Type | Viscosity (cps) | Hydrophilic foam | Gel retention rate (%) |
| --- | --- | --- | --- |
| Aquagel | 193 | 1 | 137 |
| Aquagel | 215 | 1 | 460 |
| Aquagel | 215 | 2 | 1909 |
| Aquagel | 320 | 1 | 114 |
| Aquagel | 376 | 1 | 110 |
| Aquagel | 402 | 1 | 990 |
| Aquagel | 402 | 2 | 2202 |
| O/W gel | 208 | 1 | 110 |
| O/W gel | 312 | 1 | 119 |
| O/W gel | 386 | 1 | 95 |

As can be seen in Table 3, with respect to an aquagel having a viscosity of about 402 cps, the gel retention rate of the hydrophilic foam according to the embodiments of the present disclosure may have a gel retention rate of about 22.02 grams of gel per gram of the hydrophilic foam.

According to embodiments of the present disclosure, the gel should contain active agent(s) useful for treating, managing or preventing vaginal infections or cervical cancer.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

In the present disclosure, the "effective amount of an active agent" may comprise the therapeutically effective amount and prophylactically effective amount of said active agent. A "therapeutically effective amount" of an active agent is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent. A "prophylactically effective amount" of an active agent is an amount sufficient to prevent a disease or condition, or one or more symptoms associated with the disease or condition, or prevent its recurrence. The term "prophylactically effective amount" can encompass an amount that improves overall prophylaxis or enhances the prophylactic efficacy of another prophylactic agent.

The effective amount of an active agent will vary depending on the active agent, the patient in need and its use, and can readily be determined by those of ordinary skill in the art. For example, a dosage form used in the acute treatment of a disease may contain larger amounts of one or more of the active agents it comprises than a dosage form used in the chronic treatment of the same disease. It should be noted that the dosage form of the present disclosure is transdermally administered. As such, the transdermal pharmaceutical dosage form may contain smaller amounts of one or more of the active agents it comprises than an oral dosage form used to treat the same disease.

In some embodiments of the present invention, the active agent comprised in the transdermal pharmaceutical dosage form may be at least one Chinese herbal drug selected from the group consisting of: isopsoralen, triptolide, baicalein, gallic acid, quercetin, gossypol-acetic acid, baicalin, berberine hydrochloride and derivatives thereof.

The efficacies of these Chinese herbal drugs for reducing the activity of a cervical cancer cell in a subject and for reducing the viral activity of a human papilloma virus in a virus-infected cell or a virus-infected subject are disclosed in U.S. patent application Ser. No. 12/323,008 filed on Nov. 25, 2008 and entitled "Plant Derived Compounds And Compound Formulae Containing The Same For The Treatment Of Cervical Cancer."

Generally, each of the Chinese herbal drugs may be present in the gel in an amount of about 0.01-5 wt %. Specifically, the amount of the isopsoralen and derivatives thereof may be about 0.05-2.5 wt %; the amount of the triptolide and derivatives thereof may be about 0.01-0.3 wt %; the amount of the baicalein and derivatives thereof may be about 0.1-5 wt %; the amount of the gallic acid and derivatives thereof may be about 0.01-0.5 wt %; the amount of the quercetin and derivatives thereof may be about 0.1-5 wt %; and the amount of the gossypol-acetic acid and derivatives thereof may be about 0.01-0.5 wt %.

The above-identified U.S. patent application also discloses a compound formulae exhibiting synergistic effect. For example, the compound formula may comprise at least one compound selected from the group consisting of baicalein, baicalin, berberine hydrochloride, and derivatives thereof, and at least one compound selected from the group consisting of isopsoralen, triptolide, quercetin, gossypol-acetic acid, and derivatives thereof. As such, in some optional embodiment, the active agent according to the present disclosure may comprise at least one compound selected from the group consisting of baicalein, baicalin, berberine hydrochloride, and derivatives thereof, and at least one compound selected from the group consisting of isopsoralen, triptolide, quercetin, gossypol-acetic acid, and derivatives thereof.

In some alternative embodiments, the active agent comprised in the transdermal pharmaceutical dosage form may be any of acyclovir, metronidazole, nystatin and miconazole nitrate. Each of these active agents may be present in the gel in an amount of about 1.5-6.5 mg/mL.

Acyclovir (ACY) is a guanosine analogue antiviral drug primarily used for the treatment of herpes simplex virus infections. Acyclovir is commonly marketed as tablets (200 mg, 400 mg, 800 mg or 1 gram), topical and/or intravaginal cream (50 mg/g) and ointment (30 mg/g), and intravenous injection (25 mg/mL).

Metronidazole (MTZ) is a nitroimidazole anti-infective medication used mainly in the treatment of infections caused by anaerobic bacteria and protozoa. Metronidazole is commonly marketed as tablets (200 mg, 250 mg, 400 mg, or 500 mg), and gel (7.5 mg/g or 10 mg/g) for intravaginal use.

Nystatin (NYS) is a polyene antifungal drug used for the treatment of molds and yeast infections. Vaginal infections usually respond well to treatment with nystatin. In addition, nystatin is often used as prophylaxis in patients who are at risk for fungal infections. Nystatin may be commercially available in many dosage forms including oral tablets and drops, vaginal tablets and suppositories, and topical and/or intravaginal ointments, creams, and powders.

Miconazole (MIC) is an imidazole antifungal agent and can be used to treat vaginal thrush (yeast infection). Miconazole is marketed in various dosage forms, such as, oral gel (20 or 24 mg/g), and topical and/or intravaginal cream (20 mg/g) and pessaries (200 mg or 100 mg).

According to the principles and spirits of the present disclosure, the at least one active agent is dissolved in suitable solvent(s) and then mixed with the gel. The solubility of an active agent in any solvent depends on the solvent (oil)/water partition coefficient.

Solvent/water partition coefficient analysis was conducted to determine the solvent/water partition coefficient. Various solvent were used in the experiments; yet, only the 1-Octanol/water partition coefficients of the active agents described herein above are summarized in Table 4. The 1-Octanol/water partition coefficient is the logarithm of the ratio of 1-Octanol to water and can be expressed as [log $P_{oct/wat}$].

TABLE 4

| Drug | 1-Octanol/H2O ratio | Partition coefficient |
| --- | --- | --- |
| Acyclovir (ACY) | 0.02629 | −1.58 |
| Metronidazole (MTZ) | 1.11821 | 0.05 |
| Nystatin (NYS) | 1.98040 | 0.30 |
| Miconazole nitrate(MIC) | Insoluble in water | — |
| Baicalein | Insoluble in water | — |
| Isopsoralen | 306.85566 | 2.49 |
| Quercetin | Insoluble in water | — |
| Gallic acid | 1.85859 | 0.27 |
| Triptolide | 54.12816 | 1.73 |
| Gossypol-acetic acid | Insoluble in water | — |

Active agents with higher partition coefficient usually tend to dissolve in lipophilic solvents rather than hydrophilic solvents, whereas active agents with lower partition coefficient usually tend to dissolve in hydrophilic solvents rather than lipophilic solvents. Suitable solvent(s) can be selected based on the solvent/water partition coefficient thereof.

In the following working examples, active compounds were dissolved in suitable solvent to form a solution. The solution was admixed with the aquagel or O/W gel described hereinabove to afford an active agent-containing gel. In the comparative example, commercially available vaseline ointment was admixed with heptane to form vaseline gel, and the solution was also admixed with the vaseline gel. Transmembrane penetration analysis was conducted to study the transmembrane penetration behaviors of the active compounds carried in various gels.

In the transmembrane penetration analysis, swine endometrium was used as the membrane. The swine endometrium of suitable size was disposed between an upper container and a lower container. The lower container was filled with physiologic saline and debubbled. About 0.25 mL of the active agent-containing gel was added into the upper container; then, the gel was stirred (T0) for 24 hours. At 1, 2, 3, 5, 7, 9, 10.5, 24 and 26 hours after T0, about 0.45 μm of the saline was pipetted from the lower container, and the lower container was replenish with fresh saline. The pipetted sample was analyzed with HPLC-PDA system. (HPLC: Waters 2690; Detector: Waters 996 Photodiode Array Detector; Column INTERTSIL® OSD-3, 5 μm, 4.6*250 mm; Column Temperature: 25° C.; Mobile phase: Water/Acetonitrile; Scan range: 210-400 nm.)

In addition, about 0.25 mL of each gel was admixed with about 5.5 mL of saline. The admixture was extracted, filtered through a filter film (0.45 μm) and then analyzes by HPLE-PDA. The results (referred to as the "true value" hereinafter) thus obtained were regarded as the amount of a completely penetrated active agent present in the lower container. The true value of an active agent was used as the base for calculating the penetration ratio of the active agent in the working and comparative examples.

The active agents contained in the gels and the compositions of the gels were summarized in Table 5, whereas the results of the transmembrane penetration analysis were presented in Table 6.

TABLE 5

| | Working Example 3 | Working Example 4 | Comparative Example D |
| --- | --- | --- | --- |
| Gel Composition | Aqua gel: 3.069 g Water 0.186 g PEG 0.042 g MD12 0.015 g HEC | O/W gel: 2.613 g Water 0.180 g 3-Mix oil 0.183 g Silicone oil 0.152 g MD12 | Vaseline gel (3 mL): Vaseline ointment admixed with heptane to reach a viscosity of about 750 cps. |
| Active Agents | ACY: 6.46 mg MTZ: 5.99 mg NYS: 6.40 mg MIC: 6.42 mg | ACY: 6.34 mg MTZ: 6.35 mg NYS: 6.19 mg MIC: 6.22 mg | ACY: 6.55 mg MTZ: 6.12 mg NYS: 6.76 mg MIC: 5.81 mg |

TABLE 6

| Time (hr) | ACY Concentration (mg/mL) | ACY Ratio (%) | MTZ Concentration (mg/mL) | MTZ Ratio (%) | NYS Concentration (mg/mL) | NYS Ratio (%) | MIC Concentration (mg/mL) | MIC Ratio (%) |
|---|---|---|---|---|---|---|---|---|
| Working Example 3 | | | | | | | | |
| 1 | 0.00597 | 5.98 | 0.01320 | 13.8 | — | — | — | — |
| 3 | 0.02142 | 21.47 | 0.03108 | 32.48 | — | — | — | — |
| 5 | 0.02964 | 29.70 | 0.3959 | 41.32 | — | — | — | — |
| 21 | 0.06289 | 63.03 | 0.6358 | 66.44 | — | — | — | — |
| 24 | 0.05863 | 58.75 | 0.5871 | 61.36 | — | — | — | — |
| 26 | 0.05983 | 59.96 | 0.5951 | 62.20 | — | — | — | — |
| True Value | 0.09979 | 100 | 0.09568 | 100 | — | — | — | — |
| Working Example 4 | | | | | | | | |
| 1-10 | — | — | — | — | — | — | — | — |
| 21 | 0.00251 | 1.83 | 0.00651 | 4.54 | 0.00193 | 2.99 | 0.00706 | 5.04 |
| 24 | 0.06050 | 44.00 | 0.06167 | 43.02 | 0.02072 | 32.14 | 0.06066 | 43.31 |
| 26 | 0.08340 | 60.67 | 0.08107 | 56.55 | 0.03007 | 46.64 | 0.08272 | 59.07 |
| True Value | 0.13748 | 100 | 0.14334 | 100 | 0.06448 | 100 | 0.14005 | 100 |
| Comparative Example D | | | | | | | | |
| 1 | — | — | — | — | — | — | — | — |
| 3 | — | — | 0.00046 | 0.295 | — | — | — | — |
| 5 | — | — | 0.00059 | 0.377 | — | — | — | — |
| 10.5 | — | — | 0.00096 | 0.613 | — | — | — | — |
| 24 | — | — | 0.00174 | 1.11 | — | — | — | — |
| 26 | — | — | 0.00143 | 0.92 | — | — | — | — |
| True Value | 0.18648 | 100 | 0.15631 | 100 | — | — | — | — |

Note:
In Table 6, "—" means there is no measurable amount of the active agent present in the pipetted sample.

As can be seen in Table 6, vaseline gel is not as a suitable carrier for delivering the active agent(s) specified herein. In addition, it is found that the efficacy of a gel for delivering an active compound may be related to the solvent/water partition coefficient of the active agent. For example, for active agents (such as ACY and MTZ) that tend to dissolve in hydrophilic solvents, aquagel can be used as a suitable carrier. However, from the result of working example 3, it is found that the aquagel is not suitable for delivering active agents (such as NYS and MIC) that tend to dissolve in lipophilic solvents. O/W gels, on the other hand, are able to deliver active agents (such as NYS and MIC) that tend to dissolve in lipophilic solvents. Besides, as the result of working example 4 shows, the O/W gel provided herein is also suitable for carrying the active agents (such as ACY and MTZ) that tend to dissolve in hydrophilic solvents.

Moreover, ASTM F 756-93 (Standard Practice for Assessment of Hemolytic Properties of Materials) analysis was conducted to determine the hemolytic properties of the gels of working examples 3 and 4. The analysis to results showed that the hemolytic index of the gel of working example 3 is 0 (non-hemolytic); whereas the hemolytic index of the gel of working example 4 is 5 (slightly hemolytic).

In some embodiments of the present disclosure, the gel has a pH of about 3-5; for example, 3, 3.5, 4, 4.5 or 5. Such pH value matches with the normal physiological condition within the vaginal canal.

Conventionally, active agents are coated in carriers such as microcapsules or liposomes. The active agents in such carriers would only be released upon the degradation or decomposition of the carriers. Hence, it takes longer time to initially release the active agents as comparing with the medication vehicle provided herein.

The gel retained in the hydrophilic foam is adherent. Hence, the gel may adhere to the vaginal mucosa and release the active agent(s) comprised therein in a sustained way. As such, the efficacy of the treatment, management and/or prevention may be improved. In addition, the main constituent of the aquagel (and the O/W gel) is water, which may moisten the vaginal canal thereby reducing the uncomfortableness experienced by the patient.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the to art could make numerous alterations to the disclosed embodiments without departing from the spirit or scope of this invention.

What is claimed is:

1. A hydrophilic foam comprising a polyurethane matrix having a plurality of cells, wherein the hydrophilic foam is prepared from a composition comprising:
    (1) 1 part by weight of water, wherein the water is a sole blowing agent of the composition;
    (2) at least one hydrophilic polyol, wherein the hydrophilic polyol is about 35-40 parts by weight of polyoxyethylene polyoxypropylene glyceryl ether, or a mixture of about 10-12 parts by weights of polyoxypropylene glyceryl ether and about 25-28 parts by weight of polyoxyethylene polyoxypropylene glyceryl ether;
    (3) an isocyanate in an amount of about 10 to 15 parts by weight, wherein the isocyanate is 4,4'-diphenylmethane diisocyanate;

(4) a catalyst in an amount of about 0.01 to 0.1 part by weight, wherein the catalyst is N-ethyl morpholine;

5) a chain extender in an amount of about 0.05 to 0.1 part by weight, wherein the chain extender is diethanolamine; and (6) a foam stabilizer in an amount of about 0.1 to 1 part by weight, wherein the foam stabilizer is a silicone surfactant; whereby the cells are capable of retaining water in an amount of about 10-20 grams of water per gram of the hydrophilic foam and retaining gel in an amount of about 1-25 grams of gel per gram of the hydrophilic foam.

2. A transdermal pharmaceutical dosage form for treating, managing or preventing vaginal infections or cervical cancer, comprising:

a hydrophilic foam of claim 1; and a gel retained within the cells of the hydrophilic foam, wherein the gel comprises an effective amount of at least one active agent, and the gel has a viscosity in a range of about 100 to 500 cps.

3. The transdermal pharmaceutical dosage form of claim 2, wherein the active agent is at least one Chinese herbal drug selected from the group consisting of: isopsoralen, triptolide, baicalein, gala acid, quercetin, gossypol-acetic acid, baicalin, berberine hydrochloride and derivatives thereof.

4. The transdermal pharmaceutical dosage form of claim 2, wherein the active agent is any of acyclovir, metronidazole, nystatin and miconazole nitrate.

* * * * *